United States Patent
Rossomando et al.

(10) Patent No.: US 10,047,150 B2
(45) Date of Patent: Aug. 14, 2018

(54) ANTI-NEUBLASTIN ANTIBODIES AND USES THEREOF

(71) Applicant: GLORIANA THERAPEUTICS SARL

(72) Inventors: Anthony Rossomando, Revere, MA (US); Ping Jin, Southborough, MA (US)

(73) Assignee: GLORIANA THERAPEUTICS SARL, Geneva (CH)

(*) Notice: Subject to any disclaimer, the term of this patent is extended or adjusted under 35 U.S.C. 154(b) by 0 days.

(21) Appl. No.: 14/589,372

(22) Filed: Jan. 5, 2015

(65) Prior Publication Data

US 2015/0344550 A1  Dec. 3, 2015

Related U.S. Application Data

(63) Continuation of application No. 12/672,213, filed as application No. PCT/US2008/072216 on Aug. 5, 2008, now abandoned.

(60) Provisional application No. 60/954,746, filed on Aug. 8, 2007.

(51) Int. Cl.
    *C07K 16/18*  (2006.01)
    *G01N 33/68*  (2006.01)
    *C07K 16/22*  (2006.01)

(52) U.S. Cl.
    CPC ........... *C07K 16/18* (2013.01); *C07K 16/22* (2013.01); *G01N 33/6827* (2013.01); *C07K 2317/21* (2013.01); *C07K 2317/24* (2013.01); *C07K 2317/54* (2013.01); *C07K 2317/55* (2013.01); *C07K 2317/622* (2013.01); *C07K 2317/76* (2013.01)

(58) Field of Classification Search
    CPC ........... C07K 2317/76; C07K 2317/24; C07K 16/22; C07K 2317/21; C07K 2317/55; C07K 16/18; C07K 2317/622; C07K 2317/54; G01N 33/6827
    See application file for complete search history.

(56) References Cited

PUBLICATIONS

Anonymous. XP002505115—"Monoclonal Anti-human Artemin Antibody," R&D Systems Product Data Sheets, Mar. 23, 2006.*
Kimball. Introduction to Immunology (1983), MacMillan, NY, pp. 101-102.*

* cited by examiner

*Primary Examiner* — Gregory S Emch
(74) *Attorney, Agent, or Firm* — Ann-Louise Kerner

(57) ABSTRACT

Antibodies and antigen binding fragments that bind to neublastin polypeptides are disclosed. Also disclosed are methods of using the antibodies and antigen binding fragments in assays for detecting the presence or amount of endogenous and/or exogenous neublastin in a sample and in methods of antagonizing neublastin bioactivity.

9 Claims, 3 Drawing Sheets

SEQUENCE LISTING

```
<160> NUMBER OF SEQ ID NOS: 12

<210> SEQ ID NO 1
<211> LENGTH: 113
<212> TYPE: PRT
<213> ORGANISM: Homo sapiens

<400> SEQUENCE: 1

Ala Gly Gly Pro Gly Ser Arg Ala Arg Ala Ala Gly Ala Arg Gly Cys
  1               5                  10                  15

Arg Leu Arg Ser Gln Leu Val Pro Val Arg Ala Leu Gly Leu Gly His
             20                  25                  30

Arg Ser Asp Glu Leu Val Arg Phe Arg Phe Cys Ser Gly Ser Cys Arg
         35                  40                  45

Arg Ala Arg Ser Pro His Asp Leu Ser Leu Ala Ser Leu Leu Gly Ala
     50                  55                  60

Gly Ala Leu Arg Pro Pro Pro Gly Ser Arg Pro Val Ser Gln Pro Cys
 65                  70                  75                  80

Cys Arg Pro Thr Arg Tyr Glu Ala Val Ser Phe Met Asp Val Asn Ser
                 85                  90                  95

Thr Trp Arg Thr Val Asp Arg Leu Ser Ala Thr Ala Cys Gly Cys Leu
            100                 105                 110

Gly

<210> SEQ ID NO 2
<211> LENGTH: 113
<212> TYPE: PRT
<213> ORGANISM: Artificial Sequence
<220> FEATURE:
<223> OTHER INFORMATION: Synthetically generated peptide

<400> SEQUENCE: 2

Ala Gly Gly Pro Gly Ser Arg Ala Arg Ala Ala Gly Ala Arg Gly Cys
  1               5                  10                  15

Arg Leu Arg Ser Gln Leu Val Pro Val Arg Ala Leu Gly Leu Gly His
             20                  25                  30

Arg Ser Asp Glu Leu Val Arg Phe Arg Phe Cys Ser Gly Ser Cys Glu
         35                  40                  45

Arg Ala Arg Ser Pro His Asp Leu Ser Leu Ala Ser Leu Leu Gly Ala
     50                  55                  60

Gly Ala Leu Arg Pro Pro Pro Gly Ser Arg Pro Val Ser Gln Pro Cys
 65                  70                  75                  80
```

```
Cys Arg Pro Thr Arg Tyr Glu Ala Val Ser Phe Met Asp Val Asn Ser
                85                  90                  95
Thr Trp Arg Thr Val Asp Arg Leu Ser Ala Thr Ala Cys Gly Cys Leu
            100                 105                 110
Gly
```

<210> SEQ ID NO 3
<211> LENGTH: 113
<212> TYPE: PRT
<213> ORGANISM: Artificial Sequence
<220> FEATURE:
<223> OTHER INFORMATION: Synthetically generated peptide

<400> SEQUENCE: 3

```
Ala Gly Gly Pro Gly Ser Arg Ala Arg Ala Ala Gly Ala Arg Gly Cys
 1               5                  10                  15
Arg Leu Arg Ser Gln Leu Val Pro Val Arg Ala Leu Gly Leu Gly His
                20                  25                  30
Arg Ser Asp Glu Leu Val Arg Phe Arg Phe Cys Ser Gly Ser Cys Arg
             35                  40                  45
Glu Ala Arg Ser Pro His Asp Leu Ser Leu Ala Ser Leu Leu Gly Ala
 50                  55                  60
Gly Ala Leu Arg Pro Pro Gly Ser Arg Pro Val Ser Gln Pro Cys
 65                  70                  75                  80
Cys Arg Pro Thr Arg Tyr Glu Ala Val Ser Phe Met Asp Val Asn Ser
                85                  90                  95
Thr Trp Arg Thr Val Asp Arg Leu Ser Ala Thr Ala Cys Gly Cys Leu
            100                 105                 110
Gly
```

<210> SEQ ID NO 4
<211> LENGTH: 113
<212> TYPE: PRT
<213> ORGANISM: Artificial Sequence
<220> FEATURE:
<223> OTHER INFORMATION: Synthetically generated peptide

<400> SEQUENCE: 4

```
Ala Gly Gly Pro Gly Ser Arg Ala Arg Ala Ala Gly Ala Arg Gly Cys
 1               5                  10                  15
Arg Leu Arg Ser Gln Leu Val Pro Val Arg Ala Leu Gly Leu Gly His
                20                  25                  30
Arg Ser Asp Glu Leu Val Arg Phe Arg Phe Cys Ser Gly Ser Cys Arg
             35                  40                  45
Arg Ala Glu Ser Pro His Asp Leu Ser Leu Ala Ser Leu Leu Gly Ala
 50                  55                  60
Gly Ala Leu Arg Pro Pro Gly Ser Arg Pro Val Ser Gln Pro Cys
 65                  70                  75                  80
Cys Arg Pro Thr Arg Tyr Glu Ala Val Ser Phe Met Asp Val Asn Ser
                85                  90                  95
Thr Trp Arg Thr Val Asp Arg Leu Ser Ala Thr Ala Cys Gly Cys Leu
            100                 105                 110
Gly
```

<210> SEQ ID NO 5
<211> LENGTH: 113
<212> TYPE: PRT
<213> ORGANISM: Artificial Sequence
<220> FEATURE:
<223> OTHER INFORMATION: Synthetically generated peptide

<400> SEQUENCE: 5

```
Ala Gly Gly Pro Gly Ser Arg Ala Arg Ala Ala Gly Ala Arg Gly Cys
 1               5                  10                  15

Arg Leu Arg Ser Gln Leu Val Pro Val Arg Ala Leu Gly Leu Gly His
            20                  25                  30

Arg Ser Asp Glu Leu Val Arg Phe Arg Phe Cys Ser Gly Ser Cys Glu
        35                  40                  45

Glu Ala Arg Ser Pro His Asp Leu Ser Leu Ala Ser Leu Leu Gly Ala
    50                  55                  60

Gly Ala Leu Arg Pro Pro Gly Ser Arg Pro Val Ser Gln Pro Cys
65                  70                  75                  80

Cys Arg Pro Thr Arg Tyr Glu Ala Val Ser Phe Met Asp Val Asn Ser
                85                  90                  95

Thr Trp Arg Thr Val Asp Arg Leu Ser Ala Thr Ala Cys Gly Cys Leu
            100                 105                 110

Gly
```

<210> SEQ ID NO 6
<211> LENGTH: 99
<212> TYPE: PRT
<213> ORGANISM: Artificial Sequence
<220> FEATURE:
<223> OTHER INFORMATION: Synthetically generated peptide

<400> SEQUENCE: 6

```
Gly Cys Arg Leu Arg Ser Gln Leu Val Pro Val Arg Ala Leu Gly Leu
 1               5                  10                  15

Gly His Arg Ser Asp Glu Leu Val Arg Phe Arg Phe Cys Ser Gly Ser
            20                  25                  30

Cys Glu Glu Ala Arg Ser Pro His Asp Leu Ser Leu Ala Ser Leu Leu
        35                  40                  45

Gly Ala Gly Ala Leu Arg Pro Pro Gly Ser Arg Pro Val Ser Gln
    50                  55                  60

Pro Cys Cys Arg Pro Thr Arg Tyr Glu Ala Val Ser Phe Met Asp Val
65                  70                  75                  80

Asn Ser Thr Trp Arg Thr Val Asp Arg Leu Ser Ala Thr Ala Cys Gly
                85                  90                  95

Cys Leu Gly
```

<210> SEQ ID NO 7
<211> LENGTH: 104
<212> TYPE: PRT
<213> ORGANISM: Artificial Sequence
<220> FEATURE:
<223> OTHER INFORMATION: Synthetically generated peptide

<400> SEQUENCE: 7

```
Ala Ala Gly Ala Arg Gly Cys Arg Leu Arg Ser Gln Leu Val Pro Val
 1               5                  10                  15

Arg Ala Leu Gly Leu Gly His Arg Ser Asp Glu Leu Val Arg Phe Arg
            20                  25                  30

Phe Cys Ser Gly Ser Cys Glu Glu Ala Arg Ser Pro His Asp Leu Ser
        35                  40                  45

Leu Ala Ser Leu Leu Gly Ala Gly Ala Leu Arg Pro Pro Gly Ser
    50                  55                  60
```

Arg Pro Val Ser Gln Pro Cys Cys Arg Pro Thr Arg Tyr Glu Ala Val
65                  70                  75                  80

Ser Phe Met Asp Val Asn Ser Thr Trp Arg Thr Val Asp Arg Leu Ser
                85                  90                  95

Ala Thr Ala Cys Gly Cys Leu Gly
            100

<210> SEQ ID NO 8
<211> LENGTH: 113
<212> TYPE: PRT
<213> ORGANISM: Artificial Sequence
<220> FEATURE:
<223> OTHER INFORMATION: Synthetically generated peptide

<400> SEQUENCE: 8

Ala Gly Gly Pro Gly Ser Arg Ala Arg Ala Gly Ala Arg Gly Cys
1               5                   10                  15

Arg Leu Arg Ser Gln Leu Val Pro Val Arg Ala Leu Gly Leu Gly His
            20                  25                  30

Arg Ser Asp Glu Leu Val Arg Phe Arg Phe Cys Ser Gly Ser Cys Arg
        35                  40                  45

Glu Ala Glu Ser Pro His Asp Leu Ser Leu Ala Ser Leu Leu Gly Ala
    50                  55                  60

Gly Ala Leu Arg Pro Pro Gly Ser Arg Pro Val Ser Gln Pro Cys
65                  70                  75                  80

Cys Arg Pro Thr Arg Tyr Glu Ala Val Ser Phe Met Asp Val Asn Ser
                85                  90                  95

Thr Trp Arg Thr Val Asp Arg Leu Ser Ala Thr Ala Cys Gly Cys Leu
            100                 105                 110

Gly

<210> SEQ ID NO 9
<211> LENGTH: 113
<212> TYPE: PRT
<213> ORGANISM: Artificial Sequence
<220> FEATURE:
<223> OTHER INFORMATION: Synthetically generated peptide

<400> SEQUENCE: 9

Ala Gly Gly Pro Gly Ser Arg Ala Arg Ala Gly Ala Arg Gly Cys
1               5                   10                  15

Arg Leu Arg Ser Gln Leu Val Pro Val Arg Ala Leu Gly Leu Gly His
            20                  25                  30

Arg Ser Asp Glu Leu Val Arg Phe Arg Phe Cys Ser Gly Ser Cys Glu
        35                  40                  45

Arg Ala Glu Ser Pro His Asp Leu Ser Leu Ala Ser Leu Leu Gly Ala
    50                  55                  60

Gly Ala Leu Arg Pro Pro Gly Ser Arg Pro Val Ser Gln Pro Cys
65                  70                  75                  80

Cys Arg Pro Thr Arg Tyr Glu Ala Val Ser Phe Met Asp Val Asn Ser
                85                  90                  95

Thr Trp Arg Thr Val Asp Arg Leu Ser Ala Thr Ala Cys Gly Cys Leu
            100                 105                 110

Gly

<210> SEQ ID NO 10
<211> LENGTH: 220

<212> TYPE: PRT
<213> ORGANISM: Homo sapiens

<400> SEQUENCE: 10

Met Glu Leu Gly Leu Gly Gly Leu Ser Thr Leu Ser His Cys Pro Trp
1               5                   10                  15

Pro Arg Arg Gln Pro Ala Leu Trp Pro Thr Leu Ala Ala Leu Ala Leu
            20                  25                  30

Leu Ser Ser Val Ala Glu Ala Ser Leu Gly Ser Ala Pro Arg Ser Pro
        35                  40                  45

Ala Pro Arg Glu Gly Pro Pro Val Leu Ala Ser Pro Ala Gly His
    50                  55                  60

Leu Pro Gly Gly Arg Thr Ala Arg Trp Cys Ser Gly Arg Ala Arg Arg
65                  70                  75                  80

Pro Pro Pro Gln Pro Ser Arg Pro Ala Pro Pro Pro Ala Pro Pro
                85                  90                  95

Ser Ala Leu Pro Arg Gly Gly Arg Ala Ala Arg Ala Gly Gly Pro Gly
                100                 105                 110

Ser Arg Ala Arg Ala Ala Gly Ala Arg Gly Cys Arg Leu Arg Ser Gln
            115                 120                 125

Leu Val Pro Val Arg Ala Leu Gly Leu Gly His Arg Ser Asp Glu Leu
        130                 135                 140

Val Arg Phe Arg Phe Cys Ser Gly Ser Cys Arg Arg Ala Arg Ser Pro
145                 150                 155                 160

His Asp Leu Ser Leu Ala Ser Leu Leu Gly Ala Gly Ala Leu Arg Pro
                165                 170                 175

Pro Pro Gly Ser Arg Pro Val Ser Gln Pro Cys Cys Arg Pro Thr Arg
            180                 185                 190

Tyr Glu Ala Val Ser Phe Met Asp Val Asn Ser Thr Trp Arg Thr Val
        195                 200                 205

Asp Arg Leu Ser Ala Thr Ala Cys Gly Cys Leu Gly
    210                 215                 220

<210> SEQ ID NO 11
<211> LENGTH: 224
<212> TYPE: PRT
<213> ORGANISM: Mus musculus

<400> SEQUENCE: 11

Met Glu Leu Gly Leu Ala Glu Pro Thr Ala Leu Ser His Cys Leu Arg
1               5                   10                  15

Pro Arg Trp Gln Ser Ala Trp Trp Pro Thr Leu Ala Val Leu Ala Leu
            20                  25                  30

Leu Ser Cys Val Thr Glu Ala Ser Leu Asp Pro Met Ser Arg Ser Pro
        35                  40                  45

Ala Ala Arg Asp Gly Pro Ser Pro Val Leu Ala Pro Thr Asp His
    50                  55                  60

Leu Pro Gly Gly His Thr Ala His Leu Cys Ser Glu Arg Thr Leu Arg
65                  70                  75                  80

Pro Pro Pro Gln Ser Pro Gln Pro Ala Pro Pro Pro Gly Pro Ala
                85                  90                  95

Leu Gln Ser Pro Pro Ala Ala Leu Arg Gly Ala Arg Ala Ala Arg Ala
            100                 105                 110

Gly Thr Arg Ser Ser Arg Ala Arg Thr Thr Asp Ala Arg Gly Cys Arg
        115                 120                 125

```
Leu Arg Ser Gln Leu Val Pro Val Ser Ala Leu Gly Leu Gly His Ser
    130                 135                 140

Ser Asp Glu Leu Ile Arg Phe Arg Phe Cys Ser Gly Ser Cys Arg Arg
145                 150                 155                 160

Ala Arg Ser Gln His Asp Leu Ser Leu Ala Ser Leu Leu Gly Ala Gly
                165                 170                 175

Ala Leu Arg Ser Pro Pro Gly Ser Arg Pro Ile Ser Gln Pro Cys Cys
            180                 185                 190

Arg Pro Thr Arg Tyr Glu Ala Val Ser Phe Met Asp Val Asn Ser Thr
            195                 200                 205

Trp Arg Thr Val Asp His Leu Ser Ala Thr Ala Cys Gly Cys Leu Gly
            210                 215                 220

<210> SEQ ID NO 12
<211> LENGTH: 224
<212> TYPE: PRT
<213> ORGANISM: Rattus norvegicus

<400> SEQUENCE: 12

Met Glu Leu Gly Leu Gly Glu Pro Thr Ala Leu Ser His Cys Leu Arg
1               5                   10                  15

Pro Arg Trp Gln Pro Ala Leu Trp Pro Thr Leu Ala Ala Leu Ala Leu
            20                  25                  30

Leu Ser Ser Val Thr Glu Ala Ser Leu Asp Pro Met Ser Arg Ser Pro
        35                  40                  45

Ala Ser Arg Asp Val Pro Ser Pro Val Leu Ala Pro Pro Thr Asp Tyr
    50                  55                  60

Leu Pro Gly Gly His Thr Ala His Leu Cys Ser Glu Arg Thr Leu Arg
65                  70                  75                  80

Pro Pro Pro Gln Ser Pro Gln Pro Ala Pro Pro Pro Gly Pro Pro Ala
                85                  90                  95

Leu Gln Ser Pro Pro Ala Ala Leu Arg Gly Ala Arg Ala Ala Arg Ala
            100                 105                 110

Gly Thr Arg Ser Ser Arg Ala Arg Ala Thr Asp Ala Arg Gly Cys Arg
            115                 120                 125

Leu Arg Ser Gln Leu Val Pro Val Ser Ala Leu Gly Leu Gly His Ser
    130                 135                 140

Ser Asp Glu Leu Ile Arg Phe Arg Phe Cys Ser Gly Ser Cys Arg Arg
145                 150                 155                 160

Ala Arg Ser Pro His Asp Leu Ser Leu Ala Ser Leu Leu Gly Ala Gly
                165                 170                 175

Ala Leu Arg Ser Pro Pro Gly Ser Arg Pro Ile Ser Gln Pro Cys Cys
            180                 185                 190

Arg Pro Thr Arg Tyr Glu Ala Val Ser Phe Met Asp Val Asn Ser Thr
            195                 200                 205

Trp Arg Thr Val Asp His Leu Ser Ala Thr Ala Cys Gly Cys Leu Gly
            210                 215                 220
```

ANTI-NEUBLASTIN ANTIBODIES AND USES THEREOF

TECHNICAL FIELD

The invention relates to antibodies and antibody fragments that bind to neublastin.

BACKGROUND

Neublastin, also known as artemin and enovin, is a 24 kDa homodimeric, secreted protein that promotes the outgrowth and survival of neurons of the peripheral and central nervous system (Baudet et al., 2000, *Development*, 127:4335; Masure et al., 1999, *Eur. J. Biochem.*, 266:892; Rosenblad et al., 2000, *Mol. Cell Neurosci.*, 15(2):199). Neublastin mRNA is expressed predominantly in embryonic kidney and lung, and in adults, is expressed highest in pituitary gland, trachea, and placenta (Baudet et al., 2000, *Development*, 127:4335).

Neublastin is a member of the glial cell line-derived neurotrophic factor (GDNF) ligand family. GDNF ligands activate both Ras and phosphatidylinositol-3-kinase signal transduction pathways by engaging the membrane-bound c-RET receptor tyrosine kinase. This c-RET-mediated signaling requires an additional co-receptor, a glycosylphosphatidyl inositol (GPI)-anchored GDNF family receptor alpha (GFRalpha) protein, which confers ligand specificity to c-RET. Four GFRalpha co-receptor proteins have been identified (GFRalpha-4). Neublastin shows highest affinity for GFRalpha3 in vitro, however in studies using human fibroblasts, neublastin can stimulate c-RET-dependent signaling through either GFRalpha3 or GFRalpha1 (Baudet et al., 2000, Development, 127:4335; Masure et al., 1999, *Eur. J. Biochem.* 266:892; Rosenblad et al., 2000, Mol. Cell Neurosci., 15(2):199).

The neublastin/c-RET/GFRalpha3 ternary complex is localized predominantly to nociceptive sensory neurons that detect pain and injury (Orozco et al., 2001, *Eur. J. Neurosci.*, 13(11):2177). Neublastin thus has potential clinical application in the treatment of neuropathy and more specifically in the treatment of neuropathic pain. In addition, neublastin and GFRalpha3/RET are expressed at enhanced levels in pancreatic cancer tissues and neublastin promotes pancreatic cancer cell invasion (Ceyhan et al., 2006, Annals of Surgery, 244:274).

SUMMARY

The invention is based, at least in part, on the discovery of anti-neublastin antibodies that are useful in detecting endogenous and/or exogenous neublastin polypeptides and in antagonizing neublastin bioactivity.

In one aspect, the invention features an isolated antibody or antigen-binding fragment thereof that selectively binds to the polypeptide of SEQ ID NO:1 on the same epitope as the antibody produced by the hybridoma deposited in the ATCC under Accession No. PTA-7624 or PTA-7625.

Also disclosed is an isolated antibody or antigen-binding fragment thereof that selectively binds to the polypeptide of SEQ ID NO:1 and crossblocks binding of the antibody produced by the hybridoma deposited in the ATCC under Accession No. PTA-7624 or PTA-7625.

Also disclosed is an antibody produced by the hybridoma deposited in the ATCC under Accession No. PTA-7624 or PTA-7625. An antibody or antigen-binding fragment thereof can optionally contain the antigen-binding portion of an antibody produced by the hybridoma deposited in the ATCC under Accession No. PTA-7624 or PTA-7625.

The term "isolated" refers to a molecule that is substantially free of its natural environment. For instance, an isolated antibody is substantially free of cellular material from the cell or tissue source from which it was derived. The term also refers to preparations where the isolated antibody is sufficiently pure for a pharmaceutical composition, or at least 70-80% (w/w) pure, at least 80-90% (w/w) pure, at least 90-95% (w/w) pure, or at least 95%, 96%, 97%, 98%, 99%, or 100% (w/w) pure.

The term "antibody or antigen-binding fragment thereof" encompasses proteins that include at least one immunoglobulin variable region, e.g., an amino acid sequence that provides an immunoglobulin variable domain or immunoglobulin variable domain sequence. For example, the term includes an antigen-binding protein that has a heavy (H) chain variable region (abbreviated herein as VH), and a light (L) chain variable region (abbreviated herein as VL). In another example, the term includes an antigen binding protein that includes two heavy (H) chain variable regions and two light (L) chain variable regions. The term encompasses antigen-binding fragments of antibodies (e.g., single chain antibodies, Fab fragments, F(ab')2 fragments, Fd fragments, Fv fragments, and dAb fragments) as well as complete antibodies, e.g., intact immunoglobulins of types IgA, IgG, IgE, IgD, IgM (as well as subtypes thereof). The light chains of the immunoglobulin may be of types kappa or lambda. In some embodiments, the antibody is glycosylated. An antibody can be functional for antibody-dependent cytotoxicity and/or complement-mediated cytotoxicity, or may be non-functional for one or both of these activities. The VH and VL regions can be further subdivided into regions of hypervariability, termed "complementarity determining regions" ("CDR"), interspersed with regions that are more conserved, termed "framework regions" (FR). The extent of the FR's and CDR's has been precisely defined (see, Kabat, E. A., et al. (1991) Sequences of Proteins of Immunological Interest, Fifth Edition, US Department of Health and Human Services, NIH Publication No. 91-3242; and Chothia, C. et al. (1987) J. Mol. Biol. 196:901-917). Kabat definitions are used herein. Each VH and VL is typically composed of three CDR's and four FR's, arranged from amino-terminus to carboxyl-terminus in the following order: FR1, CDR1, FR2, CDR2, FR3, CDR3, FR4.

The term "selectively binds" refers to two molecules forming a complex that is stable under physiologic conditions. Selective binding is characterized by a high affinity and a low to moderate capacity as distinguished from nonspecific binding which usually has a low affinity with a moderate to high capacity. Typically, binding is considered selective when the antibody binds with a Kd of less than 10-6 M. If necessary, nonspecific binding can be reduced without substantially affecting selective binding by varying the binding conditions.

The term "crossblocking antibody" refers to a first anti-neublastin antibody that, when bound to a neublastin polypeptide, reduces or eliminates the ability of a second anti-neublastin antibody to bind to the neublastin polypeptide (relative to binding of the second anti-neublastin antibody to the neublastin polypeptide that occurs in the absence of the first anti-neublastin antibody).

In some embodiments, an antibody or antigen-binding fragment thereof described herein is a humanized antibody.

In some embodiments, an antibody or antigen-binding fragment thereof described herein is a fully human antibody.

In some embodiments, an antibody or antigen-binding fragment thereof described herein is a monoclonal antibody.

In some embodiments, an antibody or antigen-binding fragment thereof described herein is a single chain antibody.

In some embodiments, an antibody or antigen-binding fragment thereof described herein is a polyclonal antibody, a chimeric antibody, an Fab fragment, an $F_{(ab')2}$ fragment, an $F_{ab'}$ fragment, an $F_{sc}$ fragment, or an $F_v$ fragment.

Also disclosed is an isolated cell that produces an antibody or antigen-binding fragment thereof described herein. The cell can be, for example, a fused cell (e.g., a hybridoma) obtained by fusing a mammalian B cell and myeloma cell.

Also disclosed is a conjugate containing an antibody or antigen-binding fragment thereof described herein linked to a detectable label. The detectable label can be, for example, horseradish peroxidase or alkaline phosphatase or a fluorescent or radio-labeled marker.

Also disclosed is a conjugate containing an antibody or antigen-binding fragment thereof described herein linked to a solid-phase matrix (e.g., a multi-well assay plate, sepharose, agarose, or a magnetic bead).

Also disclosed is a pharmaceutical composition containing (i) an antibody or antigen-binding fragment thereof described herein, and (ii) a pharmaceutically acceptable carrier.

In another aspect, the invention features a method of determining the presence or amount of a neublastin polypeptide in a sample, which method includes: contacting a sample with an antibody or antigen-binding fragment thereof described herein for a time sufficient for the antibody or antigen-binding fragment thereof to bind to a neublastin polypeptide, if present in the sample; and detecting the presence or amount of the antibody or antigen-binding fragment thereof bound to the neublastin polypeptide to thereby determine the presence or amount of the neublastin polypeptide in the sample. In some embodiments, the method includes additional steps of: prior to the detecting step, contacting the sample with a second antibody or antigen-binding fragment thereof that selectively binds to the polypeptide of SEQ ID NO:1 for a time sufficient for the second antibody or antigen-binding fragment thereof to bind to the neublastin polypeptide bound to an antibody or antigen-binding fragment thereof described herein; and detecting the presence or amount of the second antibody or antigen-binding fragment thereof bound to the neublastin polypeptide.

Also disclosed is a method of determining the presence or amount of a neublastin polypeptide in a sample, which method includes: contacting a sample with a first antibody or antigen-binding fragment thereof that selectively binds to the polypeptide of SEQ ID NO:1 on the same epitope as the antibody produced by the hybridoma deposited in the ATCC under Accession No. PTA-7625 for a time sufficient for the first antibody or antigen-binding fragment thereof to bind to a neublastin polypeptide, if present in the sample; contacting the sample with a second antibody or antigen-binding fragment thereof that selectively binds to the polypeptide of SEQ ID NO:1 on the same epitope as the antibody produced by the hybridoma deposited in the ATCC under Accession No. PTA-7624 for a time sufficient for the second antibody or antigen-binding fragment thereof to bind the neublastin polypeptide, if bound to the first antibody or antigen-binding fragment thereof; and detecting the presence or amount of the second antibody or antigen-binding fragment thereof bound to the neublastin polypeptide, to thereby determine the presence or amount of the neublastin polypeptide in the sample.

In some embodiments, the first antibody or antigen-binding fragment thereof selectively binds to the polypeptide of SEQ ID NO:1 and crossblocks binding of the antibody produced by the hybridoma deposited in the ATCC under Accession No. PTA-7625. In some embodiments, the first antibody is produced by the hybridoma deposited in the ATCC under Accession No. PTA-7625.

In some embodiments, the second antibody or antigen-binding fragment thereof selectively binds to the polypeptide of SEQ ID NO:1 and crossblocks binding of the antibody produced by the hybridoma deposited in the ATCC under Accession No. PTA-7624. In some embodiments, the second antibody is produced by the hybridoma deposited in the ATCC under Accession No. PTA-7624.

Also disclosed is a method of determining the presence or amount of a neublastin polypeptide in a sample, which method includes: contacting a sample with a first antibody or antigen-binding fragment thereof that selectively binds to the polypeptide of SEQ ID NO:1 on the same epitope as the antibody produced by the hybridoma deposited in the ATCC under Accession No. PTA-7625 for a time sufficient for the first antibody or antigen-binding fragment thereof to bind to a neublastin polypeptide, if present in the sample; contacting the sample with a second antibody or antigen-binding fragment thereof that selectively binds to the polypeptide of SEQ ID NO:1 on the same epitope as the antibody produced by the hybridoma deposited in the ATCC under Accession No. PTA-7625 for a time sufficient for the second antibody or antigen-binding fragment thereof to bind to the neublastin polypeptide, if bound to the first antibody or antigen-binding fragment thereof; and detecting the presence or amount of the second antibody or antigen-binding fragment thereof bound to the neublastin polypeptide, to thereby determine the presence or amount of the neublastin polypeptide in the sample.

In some embodiments, the first antibody or antigen-binding fragment thereof selectively binds to the polypeptide of SEQ ID NO:1 and crossblocks binding of the antibody produced by the hybridoma deposited in the ATCC under Accession No. PTA-7625. In some embodiments, the first antibody is produced by the hybridoma deposited in the ATCC under Accession No. PTA-7625.

In some embodiments, the second antibody or antigen-binding fragment thereof selectively binds to the polypeptide of SEQ ID NO:1 and crossblocks binding of the antibody produced by the hybridoma deposited in the ATCC under Accession No. PTA-7625. In some embodiments, the second antibody is produced by the hybridoma deposited in the ATCC under Accession No. PTA-7625.

The methods described herein for determining the presence or amount of a neublastin polypeptide in a sample can optionally be performed as a sandwich-based immunoassay.

In any of the methods described herein, the sample can be obtained from a mammal (e.g., a human). The neublastin polypeptide detected according to the methods can be, for example, endogenous, wild-type neublastin or an exogenous, recombinant neublastin.

The neublastin polypeptide detected in any of the methods described herein can contain (or consist of) an amino acid sequence that is at least 80% identical (at least 90%, 95%, or 98% identical) to amino acids 15-113 of SEQ ID NO:1, wherein the polypeptide, when dimerized, binds to a complex containing GFRalpha3 and RET. In some embodiments, the neublastin polypeptide contains (or consists of) amino acids 15-113 of SEQ ID NO:1, amino acids 15-113 of SEQ ID NO:2, amino acids 15-113 of SEQ ID NO:3, amino acids 15-113 of SEQ ID NO:4, amino acids 15-113 of SEQ ID NO:5, amino acids 15-113 of SEQ ID NO:8, or amino acids 15-113 of SEQ ID NO:9. In some embodiments, the neublastin polypeptide contains (or consists of) the amino acid sequence of SEQ ID NO:1, the amino acid sequence of SEQ ID NO:2, the amino acid sequence of SEQ ID NO:3, the amino acid sequence of SEQ ID NO:4, the amino acid sequence of SEQ ID NO:5, the amino acid sequence of SEQ ID NO:8, or the amino acid sequence of SEQ ID NO:9. In some embodiments, the neublastin polypeptide contains (or consists of) amino acids 10-113 of SEQ ID NO:1.

The sample used in any of the methods described herein can be obtained from a mammal (e.g., a human) to which the neublastin polypeptide (e.g., a recombinant neublastin polypeptide) has previously been administered (e.g., by subcutaneous or intravenous administration). For example, the sample can be obtained from blood, serum, saliva, semen, urine, lacrimal fluid, or cerebral spinal fluid.

Also disclosed is a method of antagonizing neublastin activity by administering to a mammal an amount of an antibody or antigen-binding fragment thereof described herein effective to reduce or eliminate the ability of endogenous, wild-type neublastin to bind to a complex containing RET and GFRalpha3 and induce dimerization and autophosphorylation of RET. Also disclosed is the use of an antibody or antigen-binding fragment thereof described herein for the preparation of a pharmaceutical composition for antagonizing neublastin activity (by reducing or eliminating the ability of endogenous, wild-type neublastin to bind to a complex containing RET and GFRalpha3 and induce dimerization and autophosphorylation of RET).

Also disclosed is a method of treating a cancer by administering to a mammal having a cancer (e.g., a pancreatic cancer) a pharmaceutical composition containing a therapeutically effective amount of an antibody or antigen-binding fragment thereof described herein. Also disclosed is the use of an antibody or antigen-binding fragment thereof described herein for the preparation of a pharmaceutical composition for treating a cancer (e.g., a pancreatic cancer).

As used herein, the terms "to treat," "treating," and "treatment" refer to administering a therapy in an amount, manner, and/or mode effective to improve or ameliorate a symptom or parameter that characterizes a pathological condition, to reduce the severity of a symptom or parameter that characterizes a pathological condition, to prevent, slow or reverse progression of the pathological condition, or to prevent one or more symptom or parameter of the pathological condition.

The mammal treated according to the methods and uses described herein can be, e.g., a human, a mouse, a rat, a cow, a pig, a dog, a cat, or a monkey.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the exemplary methods and materials are described below. All publications, patent applications, patents, and other references mentioned herein are incorporated by reference in their entirety. In case of conflict, the present application, including definitions, will control. The materials, methods, and examples are illustrative only and not intended to be limiting.

Other features and advantages of the invention will be apparent from the following detailed description, and from the claims.

DETAILED DESCRIPTION

Figures 1, 2:
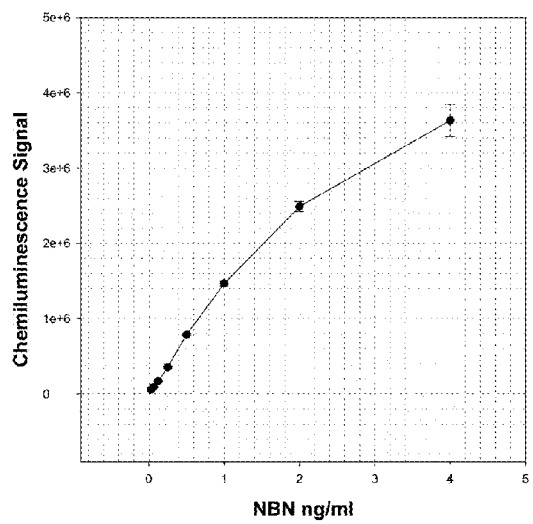
FIG. 1 is an alignment of wild-type human (SEQ ID NO:10), mouse (SEQ ID NO:11), and rat (SEQ ID NO:12) pre pro neublastin polypeptides. The left and right vertical lines indicate, respectively, the start of the mature 113 amino and 104 amino acid forms. The RRXR heparin binding motif is boxed.
FIG. 2 is a graph depicting the detection of standard concentrations of neublastin using the P3B3 assay.

Disclosed are antibodies and antigen-binding fragments thereof that bind to neublastin. The anti-neublastin antibodies are useful in assays to detect endogenous and/or exogenous neublastin polypeptides. In addition, the antibodies can be used to antagonize neublastin bioactivity and treat cancers such as pancreatic cancer.

Antibody Generation

Antibodies or antibody fragments that bind to neublastin can be generated by immunization, e.g., using an animal, or by in vitro methods such as phage display. A polypeptide that includes all or part of neublastin can be used to generate an antibody or antibody fragment. Mature, full length wild-type human neublastin contains the following amino acid sequence: AGGPGSRARAAGARGCRLRSQLVPVRAL-GLGHRSDE LVRFRFCSGSCRRARSPHDLSLASLLGA-GALRPPPGSRPVSQPCCRPTRYEAVSFMDVNS TWRT-VDRLSATACGCLG (SEQ ID NO:1). The full length mature neublastin polypeptide of SEQ ID NO:1 or a portion thereof (e.g., an amino terminal truncation containing the 25, 30, 35, 40, 45, 50, 55, 60, 65, 70, 75, 80, 85, 90, 95, 100, 105, 110, 111, or 112 carboxy terminal amino acids of the polypeptide of SEQ ID NO:1) can be used as an immunogen to generate antibodies that can be screened for reactivity to neublastin. Alternatively, a cell expressing all or part of neublastin can be used as an immunogen to generate antibodies.

In some embodiments, an immunized animal contains immunoglobulin producing cells with natural, human, or partially human immunoglobulin loci. In some embodiments, the non-human animal includes at least a part of a human immunoglobulin gene. For example, it is possible to engineer mouse strains that are deficient in mouse antibody production and contain large fragments of the human Ig loci. Using hybridoma technology, antigen-specific monoclonal antibodies derived from the genes with the desired specificity can be produced and selected. See, e.g., XenoMouse™, Green et al. Nature Genetics 7:13-21 (1994), US 2003-0070185, U.S. Pat. No. 5,789,650, and WO 96/34096.

Non-human antibodies to neublastin can also be produced, e.g., in a rodent. The non-human antibody can be humanized, e.g., as described in U.S. Pat. No. 6,602,503, EP 239 400, U.S. Pat. No. 5,693,761, and U.S. Pat. No. 6,407,213.

EP 239 400 (Winter et al.) describes altering antibodies by substitution (within a given variable region) of their CDRs for one species with those from another. CDR-substituted antibodies can be less likely to elicit an immune response in humans compared to true chimeric antibodies because the CDR-substituted antibodies contain considerably less non-human components. See Riechmann et al., 1988, Nature 332, 323-327; Verhoeyen et al., 1988, Science 239, 1534-1536. Typically, CDRs of a murine antibody are substituted into the corresponding regions in a human antibody by using recombinant nucleic acid technology to produce sequences encoding the desired substituted antibody. Human constant region gene segments of the desired isotype (e.g., gamma I for CH and kappa for CL) can be added and the humanized heavy and light chain genes can be co-expressed in mammalian cells to produce soluble humanized antibody.

WO 90/07861 describes a process that includes choosing human V framework regions by computer analysis for optimal protein sequence homology to the V region framework of the original murine antibody, and modeling the tertiary structure of the murine V region to visualize framework amino acid residues that are likely to interact with the murine CDRs. These murine amino acid residues are then superimposed on the homologous human framework. See also U.S. Pat. Nos. 5,693,762; 5,693,761; 5,585,089; and 5,530,101. Tempest et al., 1991, Biotechnology 9, 266-271 use, as standard, the V region frameworks derived from NEWM and REI heavy and light chains, respectively, for CDR-grafting without radical introduction of mouse residues. An advantage of using the Tempest et al. approach to construct NEWM and REI based humanized antibodies is that the three dimensional structures of NEWM and REI variable regions are known from x-ray crystallography and thus specific interactions between CDRs and V region framework residues can be modeled.

Non-human antibodies can be modified to include substitutions that insert human immunoglobulin sequences, e.g., consensus human amino acid residues at particular positions, e.g., at one or more (e.g., at least five, ten, twelve, or all) of the following positions: (in the framework of the variable domain of the light chain) 4L, 35L, 36L, 38L, 43L, 44L, 58L, 46L, 62L, 63L, 64L, 65L, 66L, 67L, 68L, 69L, 70L, 71L, 73L, 85L, 87L, 98L, and/or (in the framework of the variable domain of the heavy chain) 2H, 4H, 24H, 36H, 37H, 39H, 43H, 45H, 49H, 58H, 60H, 67H, 68H, 69H, 70H, 73H, 74H, 75H, 78H, 91H, 92H, 93H, and/or 103H (according to the Kabat numbering). See, e.g., U.S. Pat. No. 6,407,213.

Fully human monoclonal antibodies that bind to neublastin can be produced, e.g., using in vitro-primed human splenocytes, as described by Boerner et al., 1991, J. Immunol., 147, 86-95. They may be prepared by repertoire cloning as described by Persson et al., 1991, Proc. Nat. Acad. Sci. USA, 88: 2432-2436 or by Huang and Stollar, 1991, J. Immunol. Methods 141, 227-236; also U.S. Pat. No. 5,798,230. Large nonimmunized human phage display libraries may also be used to isolate high affinity antibodies that can be developed as human therapeutics using standard phage technology (see, e.g., Vaughan et al, 1996; Hoogenboom et al. (1998) Immunotechnology 4:1-20; and Hoogenboom et al. (2000) Immunol Today 2:371-8; US 2003-0232333).

As used herein, an "immunoglobulin variable domain sequence" refers to an amino acid sequence that can form the structure of an immunoglobulin variable domain. For example, the sequence may include all or part of the amino acid sequence of a naturally-occurring variable domain. For example, the sequence may omit one, two or more N- or C-terminal amino acids, internal amino acids, may include one or more insertions or additional terminal amino acids, or may include other alterations. In one embodiment, a polypeptide that includes an immunoglobulin variable domain sequence can associate with another immunoglobulin variable domain sequence to form a target binding structure (or "antigen binding site"), e.g., a structure that interacts with Neublastin.

The VH or VL chain of the antibody can further include all or part of a heavy or light chain constant region, to thereby form a heavy or light immunoglobulin chain, respectively. In one embodiment, the antibody is a tetramer of two heavy immunoglobulin chains and two light immunoglobulin chains. The heavy and light immunoglobulin chains can be connected by disulfide bonds. The heavy chain constant region typically includes three constant domains, CH1, CH2 and CH3. The light chain constant region typically includes a CL domain. The variable region of the heavy and light chains contains a binding domain that interacts with an antigen. The constant regions of the antibodies typically mediate the binding of the antibody to host tissues or factors, including various cells of the immune system (e.g., effector cells) and the first component (C1q) of the classical complement system.

One or more regions of an antibody can be human, effectively human, or humanized. For example, one or more of the variable regions can be human or effectively human. For example, one or more of the CDRs, e.g., heavy chain (HC) CDR1, HC CDR2, HC CDR3, light chain (LC) CDR1, LC CDR2, and LC CDR3, can be human. Each of the light chain CDRs can be human. HC CDR3 can be human. One or more of the framework regions (FR) can be human, e.g., FR1, FR2, FR3, and FR4 of the HC or LC. In some embodiments, all the framework regions are human, e.g., derived from a human somatic cell, e.g., a hematopoietic cell that produces immunoglobulins or a non-hematopoietic cell. In one embodiment, the human sequences are germline sequences, e.g., encoded by a germline nucleic acid. One or more of the constant regions can be human, effectively human, or humanized. In another embodiment, at least 70, 75, 80, 85, 90, 92, 95, or 98% of the framework regions (e.g., FR1, FR2, and FR3, collectively, or FR1, FR2, FR3, and FR4, collectively) or the entire antibody can be human, effectively human, or humanized. For example, FR1, FR2, and FR3 collectively can be at least 70, 75, 80, 85, 90, 92, 95, 98, or 99% identical to a human sequence encoded by a human germline segment.

An "effectively human" immunoglobulin variable region is an immunoglobulin variable region that includes a sufficient number of human framework amino acid positions such that the immunoglobulin variable region does not elicit an immunogenic response in a normal human. An "effectively human" antibody is an antibody that includes a sufficient number of human amino acid positions such that the antibody does not elicit an immunogenic response in a normal human.

A "humanized" immunoglobulin variable region is an immunoglobulin variable region that is modified such that the modified form elicits less of an immune response in a human than does the non-modified form, e.g., is modified to include a sufficient number of human framework amino acid positions such that the immunoglobulin variable region does not elicit an immunogenic response in a normal human. Descriptions of "humanized" immunoglobulins include, for example, U.S. Pat. No. 6,407,213 and U.S. Pat. No. 5,693,762. In some cases, humanized immunoglobulins can include a non-human amino acid at one or more framework amino acid positions.

All or part of an antibody can be encoded by an immunoglobulin gene or a segment thereof. Exemplary human immunoglobulin genes include the kappa, lambda, alpha (IgA1 and IgA2), gamma (IgG1, IgG2, IgG3, IgG4), delta, epsilon and mu constant region genes, as well as the myriad immunoglobulin variable region genes. Full-length immunoglobulin "light chains" (about 25 Kd or 214 amino acids) are encoded by a variable region gene at the NH2-terminus (about 110 amino acids) and a kappa or lambda constant region gene at the COOH-terminus. Full-length immunoglobulin "heavy chains" (about 50 Kd or 446 amino acids), are similarly encoded by a variable region gene (about 116 amino acids) and one of the other aforementioned constant region genes, e.g., gamma (encoding about 330 amino acids).

The term "antigen-binding fragment" of a full length antibody refers to one or more fragments of a full-length antibody that retain the ability to specifically bind to a target of interest (i.e., neublastin). Examples of binding fragments encompassed within the term "antigen-binding fragment" of a full length antibody include: (i) a Fab fragment, a monovalent fragment consisting of the VL, VH, CL and CH1 domains; (ii) a F(ab')2 fragment, a bivalent fragment including two Fab fragments linked by a disulfide bridge at the hinge region; (iii) a Fd fragment consisting of the VH and CH1 domains; (iv) a Fv fragment consisting of the VL and VH domains of a single arm of an antibody; (v) a dAb fragment (Ward et al., (1989) Nature 341:544-546), which consists of a VH domain; and (vi) an isolated complementarity determining region (CDR) that retains functionality. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules known as single chain Fv (scFv). See e.g., Bird et al. (1988) Science 242:423-426; and Huston et al. (1988) Proc. Natl. Acad. Sci. USA 85:5879-5883.

DEPOSITS

Hybridomas producing the monoclonal antibody P1H1.G7 and the monoclonal antibody P3B3.6 have been deposited with the American Type Culture Collection (ATCC) under the terms of the Budapest Treaty on the international Recognition of the Deposit of Microorganisms for the Purpose of Patent Procedure on Jun. 1, 2006 and bear the accession numbers ATCC PTA-7624 (P1H1.G7) and ATCC PTA-7625 (P3B3.6). Applicants assert that all restrictions imposed by the depositor on the availability to the public of the deposited material will be irrevocably removed upon the granting of the patent. Applicants acknowledge their duty to replace the deposits should the depository be unable to furnish a sample when requested due to the condition of the deposit before the end of the term of a patent issued hereon. Applicants also acknowledge their responsibility to notify the ATCC of the issuance of such a patent, at which time the deposit will be made available to the public. Prior to that time, the deposit will be made available to the Commissioner of Patents under the terms of 37 C.P.R. § 1.14 and 35 U.S.C. § 112.

Neublastin Polypeptides

Mature wild-type human neublastin is 113 amino acids in length and consists of the amino acid sequence depicted in SEQ ID NO:1. The antibodies described herein are useful in detecting endogenous and/or exogenous neublastin polypeptides. Endogenous neublastin can be, for example, the mature, wild-type human neublastin of SEQ ID NO:1, unprocessed neublastin, or a neublastin polypeptide at one of several stages of processing. In addition, or alternatively, the anti-neublastin antibodies described herein can be used to detect an exogenous neublastin polypeptide. Exogenous neublastin can contain the amino acid sequence of SEQ ID NO:1 (i.e., a sequence identical to that of naturally occurring wild-type human neublastin) or a biologically active variant thereof. A variant neublastin polypeptide can contain one or more additions, substitutions, and/or deletions, as detailed in the following sections. Wild-type neublastin polypeptides and biologically active variants thereof are collectively referred to herein as "neublastin polypeptides."

A variant neublastin polypeptide can vary in length from the corresponding wild-type polypeptide. Although the mature human neublastin polypeptide (SEQ ID NO:1) consists of the carboxy terminal 113 amino acids of pre pro neublastin (SEQ ID NO:10), not all of the 113 amino acids are required to achieve useful neublastin biological activity. Amino terminal truncation is permissible. Thus, a variant neublastin polypeptide can contain, for example, the carboxy terminal 99, 100, 101, 102, 103, 104, 105, 106, 107, 108, 109, 110, 111, 112, or 113 amino acids of SEQ ID NO:1 (i.e., its length can be 99, 100, 101, 102, 103, 104, 105, 106, 107, 108, 109, 110, 111, 112, or 113 amino acids).

A variant neublastin polypeptide can also vary in sequence from the corresponding wild-type polypeptide. In particular, certain amino acid substitutions can be introduced into the neublastin sequence without appreciable loss of a neublastin biological activity. In exemplary embodiments, a variant neublastin polypeptide (i) contains one or more amino acid substitutions, and (ii) is at least 70%, 80%, 85%, 90%, 95%, 98% or 99% identical to SEQ ID NO:1 (or 70%, 80%, 85%, 90%, 95%, 98% or 99% identical to amino acids 15-113 of SEQ ID NO:1). A variant neublastin polypeptide differing in sequence from SEQ ID NO:1 (or differing in sequence from amino acids 15-113 of SEQ ID NO:1) can include one or more amino acid substitutions (conservative or non-conservative), one or more deletions, and/or one or more insertions.

FIG. 1 is an alignment of the wild-type human, mouse, and rat pre pro neublastin polypeptides. The vertical lines in FIG. 1 indicate the start of the mature 113 amino acid form (left vertical line) and 104 amino acid form (right vertical line) of neublastin. The RRXR heparin binding motif is boxed. This alignment of naturally occurring, bioactive forms of neublastin indicates specific exemplary residues (i.e., those that are not conserved among the human, mouse, and rat forms) that can be substituted without eliminating bioactivity.

Percent identity between amino acid sequences can be determined using the BLAST 2.0 program. Sequence comparison can be performed using an ungapped alignment and using the default parameters (Blossom 62 matrix, gap existence cost of 11, per residue gap cost of 1, and a lambda ratio of 0.85). The mathematical algorithm used in BLAST programs is described in Altschul et al., 1997, *Nucleic Acids Research* 25:3389-3402.

A conservative substitution is the substitution of one amino acid for another with similar characteristics. Conservative substitutions include substitutions within the following groups: valine, alanine and glycine; leucine, valine, and isoleucine; aspartic acid and glutamic acid; asparagine and glutamine; serine, cysteine, and threonine; lysine and arginine; and phenylalanine and tyrosine. The non-polar hydrophobic amino acids include alanine, leucine, isoleucine, valine, proline, phenylalanine, tryptophan and methionine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Any substitution of one member of the above-mentioned polar, basic or acidic groups by another member of the same group can be deemed a conservative substitution.

Non-conservative substitutions include those in which (i) a residue having an electropositive side chain (e.g., Arg, His or Lys) is substituted for, or by, an electronegative residue (e.g., Glu or Asp), (ii) a hydrophilic residue (e.g., Ser or Thr) is substituted for, or by, a hydrophobic residue (e.g., Ala, Leu, Ile, Phe or Val), (iii) a cysteine or proline is substituted for, or by, any other residue, or (iv) a residue having a bulky hydrophobic or aromatic side chain (e.g., Val, Ile, Phe or Trp) is substituted for, or by, one having a smaller side chain (e.g., Ala, Ser) or no side chain (e.g., Gly).

A biologically active variant neublastin polypeptide, when dimerized, binds to a ternary complex containing GFRalpha3 and RET. Any method for detecting binding to this complex can be used to evaluate the biological activity a variant neublastin polypeptide. Exemplary assays for detecting the ternary complex-binding ability of a variant neublastin polypeptide are described in WO00/01815 (the content of which is incorporated herein by reference).

A variant neublastin polypeptide can also be assessed to evaluate its ability to trigger the neublastin signaling cascade. For example, the Kinase Receptor Activation (KIRA) assay can be used to assess the ability of a variant neublastin polypeptide to induce RET autophosphorylation (See also, Sadick et al., 1996, *Anal. Biochem.*, 235(2):207).

Substitutions at one or more of the following amino acid residues are expected to result in a variant neublastin polypeptide having reduced or absent heparin binding ability as compared to wild-type neublastin: Arg 48, Arg 49, Arg 51, Ser 46, Ser 73, Gly 72, Arg 39, Gln 21, Ser 20, Arg 68, Arg 33, His 32, Val 94, Arg 7, Arg 9, or Arg 14. Reference to a neublastin amino acid reside by position number refers to the numbering of residues relative to SEQ ID NO:1. A neublastin amino acid residue designated for substitution (e.g., an arginine residue at position 48, 49, and/or 51) can be substituted with a non-conservative amino acid residue (e.g., glutamic acid) or a conservative or amino acid residue. Exemplary amino acids that can be substituted at a residue identified herein (e.g., position 48, 49, and/or 51) include glutamic acid, aspartic acid, and alanine.

Examples of variant neublastin polypeptides that exhibit reduced or absent heparin binding are disclosed in Table 1 and in WO 2006/023781 (the content of which is incorporated herein by reference). Amino acid residues of the variant neublastin polypeptides that are mutated as compared to the corresponding wild-type position are bolded and underlined in Table 1. In addition, the neublastin polypeptide (e.g., 113, 99, or 104 amino acids in length) used as the background for the substitution is depicted in Table 1.

TABLE 1

Variant Neublastin Polypeptides

| SEQ ID NO | Position Substituted | Length of Polypeptide | Amino Acid Sequence |
|---|---|---|---|
| 2 | Arg 48 | 113 | AGGPGSRARAAGARGCRLRSQLVPVRA LGLGHRSDELVRFRFCSGSCERARSPHD LSLASLLGAGALRPPPGSRPVSQPCCRPT RYEAVSFMDVNSTWRTVDRLSATACGC LG |
| 3 | Arg 49 | 113 | AGGPGSRARAAGARGCRLRSQLVPVRA LGLGHRSDELVRFRFCSGSCREARSPHD LSLASLLGAGALRPPPGSRPVSQPCCRPT RYEAVSFMDVNSTWRTVDRLSATACGC LG |
| 4 | Arg 51 | 113 | AGGPGSRARAAGARGCRLRSQLVPVRA LGLGHRSDELVRFRFCSGSCRRAESPHD LSLASLLGAGALRPPPGSRPVSQPCCRPT RYEAVSFMDVNSTWRTVDRLSATACGC LG |
| 5 | Arg 48 and Arg 49 | 113 | AGGPGSRARAAGARGCRLRSQLVPVRA LGLGHRSDELVRFRFCSGSCEEARSPHD LSLASLLGAGALRPPPGSRPVSQPCCRPT RYEAVSFMDVNSTWRTVDRLSATACGC LG |
| 6 | Arg 48 and Arg 49 | 99 | GCRLRSQLVPVRALGLGHRSDELVRFRF CSGSCEEARSPHDLSLASLLGAGALRPPP GSRPVSQPCCRPTRYEAVSFMDVNSTW RTVDRLSATACGCLG |
| 7 | Arg 48 and Arg 49 | 104 | AAGARGCRLRSQLVPVRALGLGHRSDE LVRFRFCSGSCEEARSPHDLSLASLLGA GALRPPPGSRPVSQPCCRPTRYEAVSFM DVNSTWRTVDRLSATACGCLG |
| 8 | Arg 49 and Arg 51 | 113 | AGGPGSRARAAGARGCRLRSQLVPVRA LGLGHRSDELVRFRFCSGSCREAESPHD LSLASLLGAGALRPPPGSRPVSQPCCRPT RYEAVSFMDVNSTWRTVDRLSATACGC LG |
| 9 | Arg 48 and Arg 51 | 113 | AGGPGSRARAAGARGCRLRSQLVPVRA LGLGHRSDELVRFRFCSGSCERAESPHD |

TABLE 1-continued

Variant Neublastin Polypeptides

| SEQ ID NO | Position Substituted | Length of Polypeptide | Amino Acid Sequence |
|---|---|---|---|
| | | | LSLASLLGAGALRPPPGSRPVSQPCCRPT RYEAVSFMDVNSTWRTVDRLSATACGC LG |

A neublastin polypeptide can be optionally coupled to a polymer (e.g., a polyalkylene glycol moiety such as a polyethylene glycol moiety). In some embodiments, the polymer is coupled to the polypeptide at a site on the neublastin polypeptide that is an N terminus. In some embodiments, a variant neublastin polypeptide includes at least one amino acid substitution with respect to SEQ ID NO:1 (or with respect to amino acids 15-113 of SEQ ID NO:1), which provides an internal polymer conjugation site to which a polymer can be conjugated. In some embodiments, the polymer is coupled to a variant neublastin polypeptide at a residue (numbered in accordance with the sequence of SEQ ID NO:1) selected from the group consisting of position 14, position 39, position 68, and position 95. Exemplary neublastin variants that provide internal polymer conjugation sites are described in WO 02/060929 and WO 04/069176 (the contents of which are incorporated herein by reference).

A polypeptide can optionally contain heterologous amino acid sequences in addition to a neublastin polypeptide. "Heterologous," as used when referring to an amino acid sequence, refers to a sequence that originates from a source foreign to the particular host cell, or, if from the same host cell, is modified from its original form. Exemplary heterologous sequences include a heterologous signal sequence (e.g., native rat albumin signal sequence, a modified rat signal sequence, or a human growth hormone signal sequence) or a sequence used for purification of a neublastin polypeptide (e.g., a histidine tag). Examples of polypeptides containing a neublastin polypeptide and a heterologous signal sequence are described in US 20050158824 and WO 2004/108760.

A naturally occurring or recombinantly produced neublastin polypeptide can be isolated from cells or tissue sources using standard protein purification techniques. Alternatively, a mutated neublastin polypeptide can be synthesized chemically using standard peptide synthesis techniques. The synthesis of short amino acid sequences is described in, e.g., Stewart, et al., Solid Phase Peptide Synthesis (2d ed., 1984).

A neublastin polypeptide can be produced by recombinant DNA techniques. For example, a nucleic acid molecule encoding a neublastin polypeptide can be inserted into a vector, e.g., an expression vector, and the nucleic acid can be introduced into a cell. Suitable cells include, e.g., mammalian cells (such as human cells or CHO cells), fungal cells, yeast cells, insect cells, and bacterial cells (e.g., E. coli). When expressed in a recombinant cell, the cell can be cultured under conditions allowing for expression of a neublastin polypeptide. The neublastin polypeptide can be recovered from a cell suspension if desired. As used herein, "recovered" means that the polypeptide is removed from those components of a cell or culture medium in which it is present prior to the recovery process. The recovery process can include one or more refolding or purification steps.

Buffers and methods for inducing folding of a denatured neublastin polypeptide are described in, e.g., WO 2006/023782.

Variant neublastin polypeptides can be constructed using any of several methods known in the art. One such method is site-directed mutagenesis, in which a specific nucleotide (or, if desired a small number of specific nucleotides) is changed in order to change a single amino acid (or, if desired, a small number of predetermined amino acid residues) in the encoded variant neublastin polypeptide. Many site-directed mutagenesis kits are commercially available. One such kit is the "Transformer Site Directed Mutagenesis Kit" sold by Clontech Laboratories (Palo Alto, Calif.).

Neublastin Detection

The anti-neublastin antibodies described herein can be used in immunoassay methods to detect a neublastin polypeptide in a sample. Depending upon the anti-neublastin antibody or combination of anti-neublastin antibodies used, an assay can detect endogenous neublastin and/or an exogenous neublastin (e.g., a recombinant neublastin polypeptide). General immunoassay techniques are described in, for example, Voller et al. (1978) J. Clin. Path. 31:507-20, and Crowther (1995) Methods in Mol. Biol., Vol 42.

The anti-neublastin antibodies described herein can be used in solid-phase immunoassays. Solid-phase immunoassays generally involve the adherence or conjugation of one component (e.g., the antibody or the antigen) of the immunoassay to a solid-phase matrix (e.g., sepharose, agarose, magnetic beads, or a multi-well assay plate). For example, a neublastin polypeptide in a sample can be adhered to a solid phase matrix. Non-adherent proteins are removed by subsequent washing steps. Adherent neublastin polypeptide can then be detected by the addition of a detection antibody specific for a neublastin polypeptide. This detection antibody can be, for example, a P1H1.G7 or P3B3.6 anti-neublastin antibody described herein. In some embodiments, the antibodies can be directly coupled to a "detection moiety." Detection moieties include, for example, fluorescent labels (e.g., cy5, cy3, green fluorescent protein, or fluorescein). Detection moieties can also be radioisotope labels, such as $^{35}S$, $^{32}P$, or $^{125}I$. Detection labels can also be enzymes, e.g., alkaline phosphatase (AP), horseradish peroxidase (HRP), luciferase, or chloramphenicol acetyl transferase (CAT). Alternatively, it is often useful that the detection moiety be coupled to a secondary antibody that specifically recognizes the first, detection antibody (for example, to amplify the assay signal strength). In another embodiment, the detection antibody or secondary antibody can be conjugated to a first member of a binding pair (e.g., biotin or streptavidin) and the detection moiety can be linked to a second member of a binding pair (e.g., streptavidin or biotin).

A solid-phase immunoassay can be a "sandwich" type immunoassay, wherein a first anti-neublastin antibody (e.g., P1H1.G7 or P3B3.6) is adhered to a solid-phase matrix (e.g., sepharose, agarose, magnetic beads, or a multi-well assay plate). A neublastin polypeptide-containing sample is then added to the antibody-coupled matrix and incubated for a time sufficient to allow binding of the neublastin polypeptide (if present) to the immobilized anti-neublastin antibody. Unbound polypeptides are removed in subsequent wash steps. Neublastin polypeptides, if bound by the immobilized anti-neublastin antibody, can then be detected using a second anti-neublastin antibody. The second antibody can optionally have a different epitope specificity than the first antibody (e.g., the first antibody binds to the same epitope as P1H1.G7 and the second antibody binds to the same epitope as P3B3.6). Alternatively, the two anti-neublastin antibodies can have overlapping or identical epitope specificity (e.g., both antibodies bind to the same epitope as P3B3.6). As indicated above, the second anti-neublastin antibody can be directly coupled to a detection moiety or, alternatively, the detection moiety can be conjugated to a "secondary" antibody that is capable of recognizing the second detection antibody of the immunoassay method.

A sandwich-type immunoassay can be used to detect the presence of exogenous neublastin in a sample (e.g., a sample taken from a subject that had previously been administered a recombinant neublastin polypeptide). In an example of such an assay, the first anti-neublastin "capture" antibody is the P3B3.6 antibody or an antibody that binds to the same epitope as P3B3.6 and the second anti-neublastin "detection" antibody is the P3B3.6 antibody or an antibody that binds to the same epitope as P3B3.6. An alternative sandwich-type immunoassay can be used to detect both endogenous and exogenous neublastin in a sample. In an example of such an assay, the first anti-neublastin "capture" antibody is the P3B3.6 antibody or an antibody that binds to the same epitope as P3B3.6 and the second anti-neublastin "detection" antibody is the P1H1.G7 antibody or an antibody that binds to the same epitope as P1H1.G7.

A neublastin polypeptide can be detected via a competition-based immunoassay. Competitive inhibition assay formats generally entail the simultaneous addition of labeled analyte (e.g., detectable-label conjugated neublastin) and unlabeled analyte (e.g., neublastin from the sample). Both labeled and unlabeled analyte then compete simultaneously for the binding site on the capture antibody on the plate. Like the sequential competitive inhibition format, the colored signal is inversely proportional to the concentration of unlabeled target analyte in the sample. As above, anti-neublastin antibody is adhered to a solid phase matrix. The neublastin-containing sample, before addition to the antibody, is premixed with a known (i.e., standard) amount of neublastin competitor conjugated to a detection moiety (e.g., a "detection moiety" as described herein). Both the sample neublastin polypeptide and the neublastin-detection standard are incubated with the antibody for a time sufficient for the antibody to bind to neublastin in the sample and/or the standard. Binding of the neublastin-detection moiety standard to the antibody, and the detection signal produced by the assay, is dependent on the level of neublastin present in the sample (i.e., the higher the amount of neublastin polypeptide in a sample, the lower the signal produced in the assay). Quantitation of the amount of neublastin in a sample, can be determined by comparing the amount of signal produced by the neublastin-detection moiety standard in the absence of sample neublastin polypeptide relative to the signal produced from samples in which sample neublastin is mixed with the standard. An example of a competition-based immunoassay is the ORIGEN assay (Igen, Inc., Rockville, Md.).

A neublastin polypeptide can be detected by western blotting using the anti-neublastin antibodies described herein. Western blotting methods are described in, for example, Sambrook et al. (2001) Molecular Cloning, a Lab Manual, $3^{rd}$ Edition. A sample containing a neublastin polypeptide can be suspended in a denaturing buffer (e.g., Laemmli's buffer) containing both detergent (e.g., sodium dodecyl sulfate) and a reducing agent (e.g., DTT or beta-mercaptoethanol). The sample can then be subjected to SDS-polyacrylamide gel electrophoresis (PAGE). PAGE resolved proteins, separated by size, can then be transferred to a filter membrane (e.g., nitrocellulose) and subjected to western blot techniques using antibodies specific to neublastin. The level of neublastin in a sample can be determined by comparison to a control or reference sample containing a known amount of neublastin. In an alternative embodiment of the western technique, sometimes called a dot-blot method, the protein sample can be directly adhered to a filter membrane without prior SDS-PAGE resolution.

Immunoassays using the anti-neublastin antibodies described herein can be performed completely in solution. Examples of solution-based assays immunoassays include fluorescence resonance energy transfer (FRET)-based immunoassays, which use two detection moieties and entail the radiationless transfer of energy from a donor molecule to an acceptor molecule. The donor molecule can be a dye or chromophore that initially absorbs energy and the acceptor can be a chromophore to which the energy is subsequently transferred (called a donor/acceptor pair). This resonance interaction occurs over greater than inter-atomic distances, without conversion to thermal energy and without any molecular collision. Due to its sensitivity to distance, FRET is extremely useful in investigating protein-protein interactions and enzymatic reactions. A competition-based FRET immunoassay can be used to detect a neublastin polypeptide in a sample, wherein a specific anti-neublastin antibody is coupled to a first detection moiety (e.g., donor or acceptor molecule). The neublastin polypeptide containing sample can then be mixed with a neublastin polypeptide reference (i.e., standard) conjugated to a second detection moiety (e.g., acceptor or donor molecule where appropriate), which is also recognized by the anti-neublastin antibody and competes with the neublastin in a sample for binding to the anti-neublastin antibody. Both the sample neublastin polypeptide and the neublastin-detection standard are incubated with the antibody for a time sufficient for the antibody to bind to neublastin or the standard. Binding of the neublastin standard to the antibody, and the detection signal produced by the assay, is dependent on the level of neublastin present in the sample (i.e., the higher the amount of neublastin polypeptide in a sample, the lower the signal produced in the assay). Quantitation of the amount of neublastin in a sample can be determined by comparing the amount of signal produced by the neublastin-detection moiety standard in the absence of sample neublastin polypeptide relative to the signal produced from samples in which sample neublastin is mixed with the standard.

For purposes of detection, the donor molecule of the FRET immunoassay can be a fluorescent agent such a europium, terbium, green-fluorescent protein, or a fluorescent dye, and the acceptor molecule can be, for example, allophycocyanin (APC). These donor and acceptor molecules can be directly attached to the antibody or neublastin standards, or can be conjugated to a first member of a specific binding pair (e.g., biotin or streptavidin) and the detection moiety thus coupled to a second member of a binding pair (e.g., streptavidin or biotin).

Methods of assessing the level of a neublastin polypeptide in a sample can be quantitative, semi-quantitative, or qualitative. Thus, for example, the level of neublastin in a sample can be determined as a discrete value. For example, where quantitative immunoassays are necessary, the level of neublastin can be measured as a numerical value by correlating the detection signal derived from the quantitative assay to the detection signal of a known concentration of neublastin polypeptide or the signal presence of neublastin in a reference sample provided from a second subject. Alternatively, the level of neublastin polypeptide can be assessed using any of a variety of semi-quantitative/qualitative systems. Thus, the level of expression of neublastin polypeptide useful in the immunoassay in a sample can be expressed as, for example, (a) one or more of "excellent", "good", "satisfactory", "unsatisfactory", and/or "poor"; (b) one or more of "very high", "high", "average", "low", and/or "very low"; or (c) one or more of "++++", "+++", "++", "+", "+/−", and/or "−". In this aspect, where it is also desired, the level of neublastin polypeptide can be expressed relative to the neublastin levels of neublastin polypeptide in a reference sample from a second subject.

A neublastin-containing sample can be of unknown concentration of neublastin or a known concentration of neublastin (e.g., a neublastin standard for the assay). Assay standards, such as those useful in a neublastin immunoassay, are commonly purified proteins (e.g., a recombinant neublastin or neublastin purified from a natural source) at known concentrations, solubilized and/or diluted into an appropriate buffer used in the immunoassay (e.g., PBS, TBST, Water, HEPES). The neublastin-containing sample can be a biological fluid such as serum, blood, urine, semen, cerebral-spinal fluid, saliva, or lacrimal secretions. The sample can be obtained from a variety of sources, e.g., cell culture or a mammal (such as a mouse or a human). The neublastin-containing sample can contain exogenous and/or endogenous forms of neublastin.

Pharmaceutical Compositions

The anti-neublastin antibodies and antibody fragments described herein can be administered to a mammalian subject (e.g., a human) alone or in a mixture. For example, the antibodies and antibody fragments can be administered in the presence of a pharmaceutically acceptable excipient or carrier, such as physiological saline. The excipient or carrier can be selected on the basis of the mode and route of administration. Suitable pharmaceutical carriers are described in Remington's Pharmaceutical Sciences (E. W. Martin) and in the USP/NF (United States Pharmacopeia and the National Formulary).

A pharmaceutical composition is generally formulated to be compatible with its intended route of administration. Examples of routes of administration of an anti-neublastin antibody or antibody fragment include, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, polypropylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for adjustment of tonicity such as sodium chloride or dextrose. pH can be adjusted with acids or bases, such as hydrochloric acid or sodium hydroxide. The parenteral preparation can be enclosed in ampoules, disposable syringes, or multiple dose vials made of glass or plastic.

A pharmaceutical composition may include a "therapeutically effective amount" or a "prophylactically effective amount" of an anti-neublastin antibody or antibody fragment described herein. As used herein, "therapeutically effective amount" means an amount effective, at dosages, and for periods of time necessary, to achieve the desired therapeutic result. A therapeutically effective amount of the antibody or antibody fragment can vary according to factors such as the disease state, age, sex, and weight of the individual, and the ability of the antibody, antibody derivative, or antigen-binding polypeptide to elicit a desired response in an individual. When a therapeutically effective amount is administered, any toxic or detrimental effects of the antibody or antibody fragment are outweighed by the therapeutically beneficial effects. As used herein, "prophylactically effective amount" means an amount effective, at dosages, and for periods of time necessary, to achieve the desired prophylactic result.

Dosage regimens can be adjusted to provide the optimum desired response, e.g., a therapeutic or prophylactic response. For example, in some embodiments a single bolus is administered. In other embodiments, several divided doses are administered over time. The dose can be reduced or increased proportionately, as indicated by the exigencies of the situation. It is advantageous to formulate parenteral compositions in dosage unit form for ease of administration and uniformity of dosage. As used herein, "dosage unit form" means physically discrete units suitable as unitary dosages for the mammalian subjects to be treated, with each containing a predetermined quantity of active ingredient calculated to produce the desired therapeutic effect in association with the required pharmaceutical carrier.

Exemplary, non-limiting ranges for a therapeutically or prophylactically effective amount of an antibody or antibody fragment are 0.1-100 mg/kg, 0.5-50 mg/kg, more 1-20 mg/kg, and 1-10 mg/kg. Dosage values may vary with the type and severity of the condition being treated. For any particular subject, specific dosage regimens can be adjusted over time according to the individual need and the professional judgment of the person administering or supervising the administration of the compositions. It is to be understood that dosage ranges set forth herein are exemplary only and are not intended to limit the scope of the claimed invention.

Parenteral injectable administration can be used for subcutaneous, intramuscular, or intravenous injections and infusions. Additionally, one approach for parenteral administration employs the implantation of a slow-release or sustained-released systems, which assures that a constant level of dosage is maintained, according to U.S. Pat. No. 3,710,795, incorporated herein by reference.

Subjects intended for treatment or prophylaxis include but are not limited to humans, nonhuman primates, sheep, horses, cattle, goats, pigs, dogs, cats, rabbits, guinea pigs, hamsters, gerbils, rats, and mice.

Methods of Antagonizing Neublastin Activity

As detailed in the Examples, the P1H1.G7 and P3B3.6 monoclonal antibodies bind to neublastin and the binding of anti-neublastin monoclonal antibodies to neublastin was shown to inhibit its ability to trigger the neublastin-mediated signaling cascade and induce RET autophosphorylation. As a result, anti-neublastin antibodies described herein can be used as antagonists of neublastin bioactivity. In particular, the anti-neublastin antibodies can be administered to a mammal (e.g., a human) in an amount effective to reduce or eliminate the ability of endogenous, wild-type neublastin to bind to a complex containing RET and GFRalpha3 and induce dimerization and autophosphorylation of RET. Antagonism of neublastin bioactivity can be particularly useful in the treatment of cancers, such as pancreatic cancers where neublastin promotes cancer cell invasion. Additional exemplary cancers that can be treated with an anti-neublastin antibody or antigen-binding fragment thereof described herein include cancers of the gastrointestinal tract (e.g., esophageal or colon cancer) as well as cancers of the bladder, breast, connective tissue, kidney, lung (e.g., small cell lung carcinoma), lymph node, ovary, skin, stomach, testis, and uterus.

The following are examples of the practice of the invention. They are not to be construed as limiting the scope of the invention in any way.

EXAMPLES

Example 1: Development of Anti-Neublastin Monoclonal Antibodies

Eight week old female RBF mice (Jackson Labs, Bar Harbor, Me.) were immunized intraperitoneally with an emulsion containing either (i) a soluble Chinese Hamster Ovary (CHO) cell-expressed human neublastin (hNBN104)-hIgG1 Fc recombinant protein or (ii) an *E. coli* expressed hNBN113 molecule chemically conjugated to keyhole limpet hemocyanin (KLH). Both preparations were emulsified into Freund's complete adjuvant (FCA, Sigma Chemical Co., St. Louis, Mo.) for primary immunization and subsequently emulsified into Freund's incomplete adjuvant (IFA) for remaining booster immunizations. Further details on the protein hNBN preparations, immunizations, and hybridoma preparations are provided below.

hNBN-hIgG1 Fc protein or *E. coli* hNBN-KLH was diluted into phosphate buffered saline (PBS), pH 7.2 at a concentration of approximately 2 mg/ml. An equal volume of FCA was added to the protein prior to emulsification and immunization. For the primary immunization, each mouse was intraperitoneally administered 50 μL containing 50 μg of emulsified hNBN antigen. All subsequent immunizations were similarly dosed using either IFA or RIBI adjuvant (Sigma Chemical Co., St. Louis, Mo.). Booster immunizations were administered every two to three weeks.

Serum samples from immunized mice were collected before the first immunization, 7 days post the booster immunization, and again prior to lymphocyte cell fusions via the retro orbital plexus collection method. Serum titers were measured using an ELISA assay described below.

A mouse was selected for hybridoma development from an animal cohort immunized with the CHO expressed hNBN-IgFc. Several antibody-producing B-cell clones were derived from splenocytes isolated from this mouse. The P1H1.G7 clone produced an antibody able to bind both rat and human neublastin proteins, as determined by ELISA.

Isolated splenocytes from a mouse immunized with the *E. coli*-expressed hNBN-KLH were used to generate B-cell hybridoma lines expressing anti-neublastin antibodies. The monoclonal antibody P3B3.6 clone was selected on the basis of its ability to specifically bind to *E. coli* rat Neublastin protein. The P3B3.6 monoclonal antibody was also found to bind to human neublastin.

The development of the P1H1.G7 and P3B3.6 hybridomas is described with additional detail in the following sections.

Keyhole Limpet Hemocyanin Linkage Reaction

One-milliliter *E. coli* expressed hNBN (1.7 mg/ml in L-arg buffer) was dialyzed into MES buffer, pH 4.7 containing 0.9% NaCl. Two milligrams KLH (CalbioChem, Inc.) in similar MES buffer was mixed with the hNBN and stirred for 1 hour into a homogenous mixture. Four milligrams of ethylene dichloride (EDC, Pierce Chemical) was added to the protein mixture and allowed to mix for 2 hours at ambient temperature. The reaction was stopped by adding 100 μl saturated L-glycine (Sigma Chemical) solution and allowed to stir for 1 hour. The conjugated mixture was passed over a 30×10 ml 10 DG Econopack column (BioRad) that was equilibrated with 5 column volumes PBS. Fractions containing KLH conjugate were identified and pooled and prepared for immunizations.

Cell Lines and Media

FL653 (an APRT⁻ derivative of a Ig⁻/HGPRT⁻ Balb/c mouse myeloma cell line) and 5P2/0-Ag14 (an Ig⁻/HGPRT⁻ Balb/c mouse myeloma cell line) were each cultured in 10% fetal bovine serum in Dulbecco's modified Eagle's medium (DMEM, Sigma Chemical Co., St. Louis, Mo.) containing 4500 mg/L glucose, L-glutamine, and 20 μg/ml 8-azaguanine (Sigma Chemical Co.) for at least 10 days prior to lymphocyte cell fusion experiments. Myeloma cells were cultured in a Series II™ model water jacketed incubator (Forma Scientific, Marietta, Ohio) which had been programmed to maintain a 37° C., 98% humid environment with a 7% $CO_2$ in air atmosphere.

Solid Phase Assay (ELISA)

Maxisorp, 96-well microtiter plates (Nunc) were coated overnight with 50 ul/well of a 2 ug/ml sample of either the unconjugated *E. coli* expressed hNBN or the CHO expressed hNBN-hIgG1 Fc recombinant protein in 100 mM Sodium Phosphate Buffer, pH 8.0. Plates were emptied and washed three cycles with a solution of 0.05% Tween-20 in deionized water using an Embla automated plate washer (Skatron). Following the wash procedure, plates were filled with a 0.5% Bovine Serum Albumin (BSA) in PBS blocking solution and allowed to incubate 1 hour 37° C. Following the plate block, plates were flicked clear and 50 μl serial dilutions of serum and preserum samples from immune mice (or from monoclonal producing hybridoma supernatants) were applied to the ELISA plate and allowed to incubate 1 hour at 37° C. (diluted 1:5). Plates were washed as described above and then applied with 50 μl diluted goat anti-mouse IgG-HRP (Jackson Labs) and again allowed to incubate 1 hour at 37° C. Plates were washed followed by adding 50 μl Ultra TMB (Pierce) substrate and allowed to catalyze for approximately 10 minutes. The enzyme reaction was killed by adding equal volume 2.0 N H2SO4 and plates were read at 450 nm on a Spectramax 384 Plus (Molecular Devices) automated plate scanner. ELISA analysis was completed using Softmax Pro (Molecular Devices) absorbance analysis software.

Lymphocyte Cell Fusion

Mice that tested positive for expression of antibodies specific to either of the two neublastin antigen forms (CHO cell-expressed hNBN104 and *E. coli*-expressed hNBN113 polypeptide form) were sacrificed, and their splenic B-lymphocytes were aseptically harvested. Splenic B-lymphocytes were washed and prepared for use in PEG mediated lymphocyte somatic cell fusions, being fused to either the FL653 or SP2/0-Ag14 myeloma (Kennet, et al. 1982. Plenum Press, NY). Fused cells were plated into 24-well sterile tissue culture plates (Corning Glass Works, Corning, N.Y.) and fed with Adenine, Aminopterin and Thymidine (AAT) or Hypoxanthine, Aminopterin and Thymidine-containing culture media, for FL653 or SP2/0-Ag14 myeloma based fusions respectively. The cell culture environment was maintained at 37° C., 98% humidity and a 7.2% $CO_2$ in air atmosphere.

After 10 days, AAT or HAT resistant cultures were isolated and screened by ELISA for immunoreactivity specific to both eukaryotic and prokaryotic expression forms of the neublastin protein. Positive cultures were subsequently cloned, expanded and frozen. Cloning was performed by limiting dilution (approximately 1 cell/well) and microscopically scored upon growth to assure integrity of the selected clones. Clones that screened positive on both ELISA format assays (i.e., positive for unconjugated E. coli expressed hNBN or the CHO expressed hNBN-hIgG1 Fc recombinant protein) were expanded for freezing, subclass characterized using IsoStrip (Roche), and assayed for monoclonal production level.

Example 2: Sensitive Method for Detecting Exogenous Neublastin

In an assay termed the "P3B3 assay," a P3B3.6 antibody was used as a capturing antibody and a biotinylated P3B3.6 antibody was used for detection. This assay, which is sensitive to approximately 0.05-0.1 ng/ml and detects exogenous, recombinant neublastin but not endogenous neublastin, is described in detail below.

P3B3.6 antibodies were adhered to 96-well polystyrene assay plates (COSTAR, Corning Inc.) by incubating 50 ng/well of antibody (capture antibody) in PBS for 40 minutes at 37° C. All incubation steps were carried out with constant shaking, unless otherwise indicated. Following antibody binding, the plates were blocked with 1× casein-TBST solution (Vector Laboratories, Inc.; 0.08% casein by weight plus TBST: 25 mM Tris-HCl, pH 8.0, NaCl 125 mM, 0.1% Tween-20 by weight) and incubated for 1 hour at room temperature. The plates were washed three times with TBST at room temperature.

Recombinant neublastin (hNBN104 expressed in CHO cells) standards were prepared in normal rat serum or TBST with 0.05% bovine serum albumin (BSA) at the following concentrations: 4 ng/mL, 2 ng/mL, 1 ng/mL, 500 pg/mL, 250 pg/mL, 125 pg/mL, 62.5 pg/mL, and 31.25 pg/mL. Into each P3B3.6 antibody-coated well (each reaction), 90 μL of TBST was added along with 10 μL of one of the above neublastin standards, or test sera. The plates were incubated overnight at 4° C. Following the incubation, wells were washed three times with TBST at room temperature.

The detection antibody (biotinylated P3B3.6) was diluted to 0.2 μg/mL in 1× casein-TBST, and 100 μL of this dilute was added to each well followed by a 1 hour incubation at room temperature. The plates were then washed three times with TBST. Antibody-captured neublastin was detected using a streptavidin-conjugated horseradish peroxidase (HRP) enzyme reagent. Streptavidin-HRP was diluted 1,000 fold in 1× casein-TBST, and 100 μL was added to each well, followed by a 30 minute incubation at room temperature. The plates were washed three times with TBST. HRP enzyme substrate (Luminol/Enhancer solution and Stable Peroxide solution, Pierce Labs) was added at 100 μL per well and incubated in the dark for 1 minute. Resulting light emissions were measured using a luminometer (Tropix TR717, PE Applied Biosystems).

Figure 3:
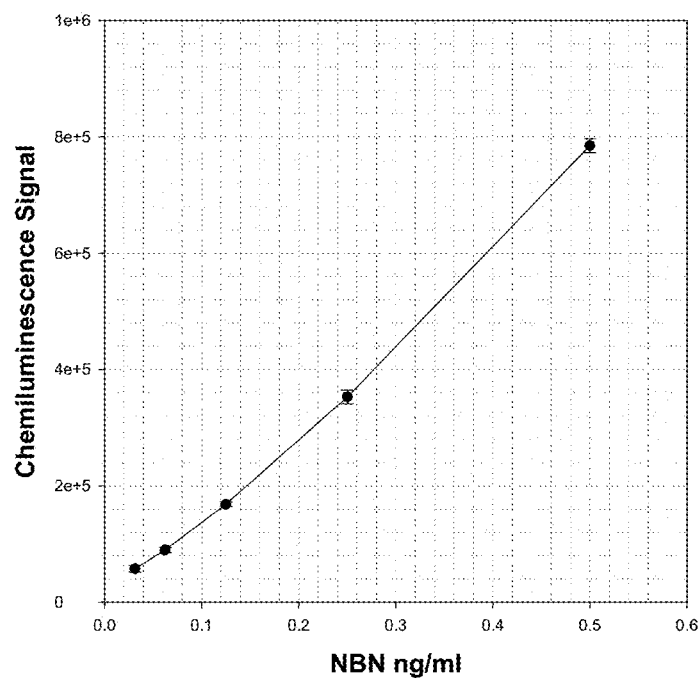
FIG. 3 is a graph depicting the linear portion of the P3B3 assay against various standard concentrations of neublastin.

Each of the three neublastin standard sample replicates was averaged and their respective standard deviation and % CV values calculated. The values from the averaged standard samples were fitted with a 4-parameter sigmoidal logistic curve (FIG. 2). When the linear portion of the P3B3 assay was expanded, the assay appeared to be linear down to 0.1 ng/ml with a potential to go as low as 0.03 ng/ml (FIG. 3).

To further explore the ability of the P3B3 assay to reproducibly identify the correct serum concentration of neublastin, an experiment was conducted to test "sham" unknowns against the neublastin standards. The concentrations of the sham unknowns were estimated from the standard curve and compared to the known amounts in each well. To determine the percentage recovery for each sham unknown, the experimentally determined values were divided by the expected values. Overall recovery averaged 104% with a standard error of +/−13%. Greatest data agreement occurred in the middle range neublastin concentrations, with outlying values predominantly occurring at neublastin concentrations below 0.125 ng/mL. Concentrations as low as 0.1 ng/mL were still within the linear range.

Figure 4:
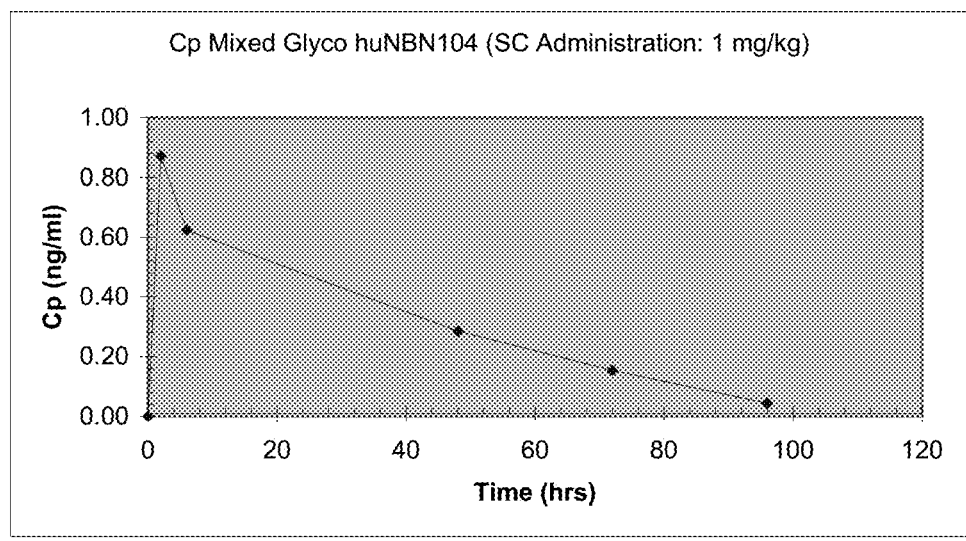
FIG. 4 is a graph depicting the kinetics of exogenous human neublastin (hNBN104 expressed in CHO cells) in rat serum following subcutaneous administration.

Example 3: Sensitive Method for Monitoring Levels of Exogenous Neublastin in an Animal Following Administration The P3B3 assay (described in Example 2) was evaluated for its ability to detect neublastin in serum. Rats were subcutaneously injected with 1 mg/kg of CHO cell-derived, recombinant human neublastin (hNBN104). At various time points post-injection, serum samples were collected and assayed for neublastin protein concentration. The assay clearly identified exogenous human neublastin that demonstrated an expected kinetic response (FIG. 4), indicating that the P3B3 assay is useful in detecting low levels of administered, recombinant human neublastin.

Example 4: Sensitive Method for Detecting Exogenous and Endogenous Neublastin

In an assay termed the "P1H1 assay," a P3B3.6 monoclonal antibody was used as a capturing antibody and a biotinylated P1H1.G7 monoclonal antibody was used for detection. Several assay parameters were evaluated using different combinations of these two monoclonals, including biotin ratios, pH, detergent, incubation time, and sample volume.

P1H1.G7 was biotinylated at three different ratios, 1:5, 1:10, and 1:20. Based on the linearity and signal to noise ratio, the 1:10 antibody to biotin ratio was chosen. Tween-20 added to the incubation buffer increased the assay's background signal in this assay. However, PBS buffer gave lower background than Hepes buffer, while pH did not seem to have a significant effect. Serum samples were incubated in P3B3.6 monoclonal antibody-coated wells for different times, ranging from 1.0 hour to overnight (about 18 hours). Overnight incubation gave better sensitivity. Different serum sample volumes ranging from 5 ul to 100 ul were tested in the assay and it was determined that 10 ul serum provided the best sensitivity of 1 ng/ml with a minimal matrix effect.

The P1H1 assay provided a sensitivity of approximately 1 ng/ml. Furthermore, the P1H1 assay was found to detect both recombinant, exogenous neublastin as well as endogenous neublastin. This contrasts with the P3B3 assay (Examples 2 and 3), which detected only exogenous neublastin.

Example 5: The Anti-hNBN P3B3.6 Antibody can Block NBN-Mediated RET Activation

Figure 5:
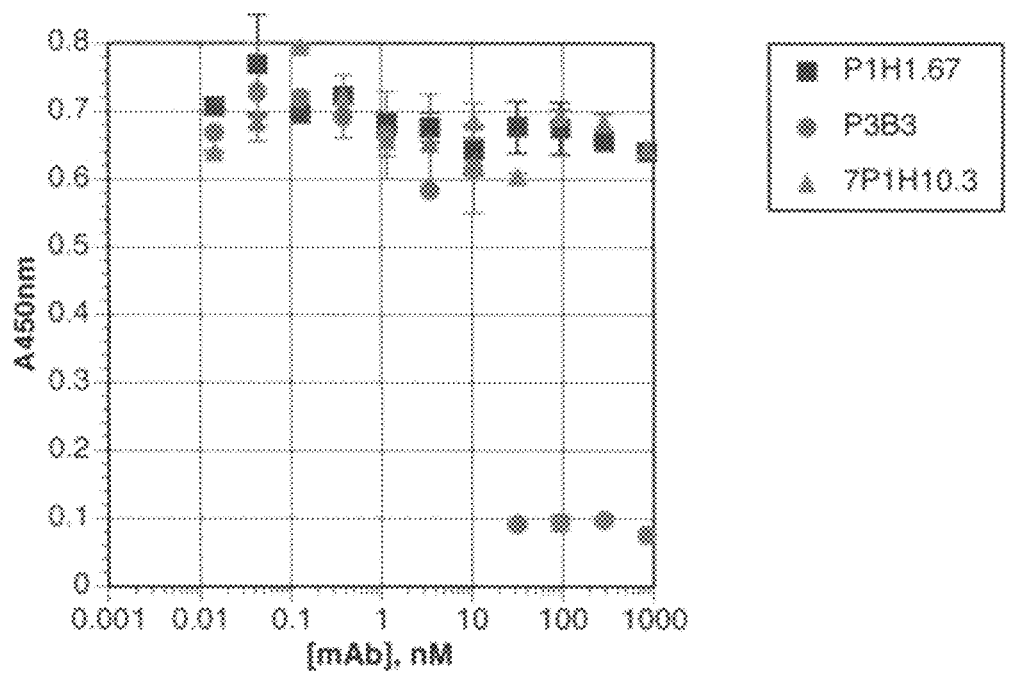
FIG. 5 is a scatter plot depicting the ability of anti-hNBN monoclonal antibodies to inhibit NBN-mediated c-RET phosphorylation in murine cells.

The anti-NBN monoclonal antibodies were evaluated for their ability to antagonize NBN-mediated RET activation in murine cells. NB41A3-mRL3 adherent murine neuroblastoma cells, which express c-RET and GFRalpha3 polypeptides, were seeded at 2×10⁵ cells/well in 24-well tissue culture plates and grown in DMEM to a confluency of 75%. Next, 75 nM samples of rat NBN were preincubated at room temperature for one hour in either DMEM alone, or in DMEM containing various concentrations (approximately 0.01 to 1,000 nM) of each of P1H1.G7 monoclonal antibody, P3B3.6 monoclonal antibody, or a control antibody (7P1H10.3). Following the preincubation, each of above rat NBN samples were added to the medium of NB41A3-mRL3 cell cultures, and inbuted with the cells for 10 minutes at 37° C. The cells were washed, lysed, and c-RET polypeptide contained in the cell lysates was captured on an ELISA plate coated with anti-RET monoclonal antibodies. Phosphorylated forms of c-RET captured on the plate were detected using a horseradish peroxidase-coupled anti-phosphotyrosine monoclonal antibody (AA.GE7.3). Preincubation of rat NBN with the P3B3.6 monoclonal antibody inhibited the ability of NBN to induce phosphorylation of c-RET in murine cells (FIG. 5). These results indicated that the P3B3.6 monoclonal antibody antagonizes NBN-mediated activation of c-RET.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An isolated monoclonal antibody, or antigen-binding fragment thereof, that selectively binds to the polypeptide of SEQ ID NO:1 and is produced by the hybridoma deposited in the ATCC under Accession No. PTA-7624 or PTA-7625.

2. The antigen-binding fragment of claim 1, which is an Fab fragment, an F(ab')2 fragment, an Fab' fragment, an Fsc fragment, or an Fv fragment.

3. A conjugate comprising the antibody, or antigen-binding fragment thereof, of claim 1 linked to a detectable label.

4. The conjugate of claim 3, wherein the detectable label is horseradish peroxidase or alkaline phosphatase.

5. The conjugate of claim 3, wherein the detectable label is a fluorescent or radio-labeled marker.

6. A pharmaceutical composition comprising the antibody, or antigen-binding fragment thereof, of claim 1 and a pharmaceutically acceptable carrier.

7. An isolated cell that produces the antibody, or antigen-binding fragment thereof, of claim 1.

8. A method of determining the presence or amount of a neublastin polypeptide in a sample, the method comprising:

contacting a sample with the antibody or antigen-binding fragment thereof of claim 1 for a time sufficient for the antibody or antigen-binding fragment thereof to bind to a neublastin polypeptide, if present in the sample; and detecting the presence or amount of the antibody or antigen-binding fragment thereof bound to the neublastin polypeptide to thereby determine the presence or amount of the neublastin polypeptide in the sample.

9. The method of claim 8, wherein the method comprises:

prior to the detecting step, contacting the sample with a second antibody or antigen-binding fragment thereof that selectively binds to the polypeptide of SEQ ID NO:1 for a time sufficient for the second antibody or antigen-binding fragment thereof to bind to the neublastin polypeptide bound to the antibody or antigen-binding fragment thereof of any one of claims 1 or 3; and detecting the presence or amount of the second antibody or antigen-binding fragment thereof bound to the neublastin polypeptide.

* * * * *